US00PP13868P39

(12) United States Plant Patent
Pieters

(10) Patent No.: US PP13,868 P3
(45) Date of Patent: Jun. 10, 2003

(54) CHRYSANTHEMUM PLANT NAMED 'GEDI ONE OST'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 1 day.

(21) Appl. No.: 09/873,601

(22) Filed: Jun. 4, 2001

(65) Prior Publication Data

US 2002/0184680 P1 Dec. 5, 2002

(51) Int. Cl.[7] ..... A01H 5/00
(52) U.S. Cl. ..... Plt./289

(58) Field of Search ..... Plt./289, 295, 286

(56) References Cited

U.S. PATENT DOCUMENTS

PP11,725 P 12/2000 Pieters ..... Plt./295

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a daisy type inflorescence, consistent flowering response to short days, blooming consistently after 49 days of short day length, free branching habit, compact growth habit, and highly floriferous plants.

1 Drawing Sheet

LATIN NAME

*Dendranthema morifolium.*

VARIETY

Figure 1:
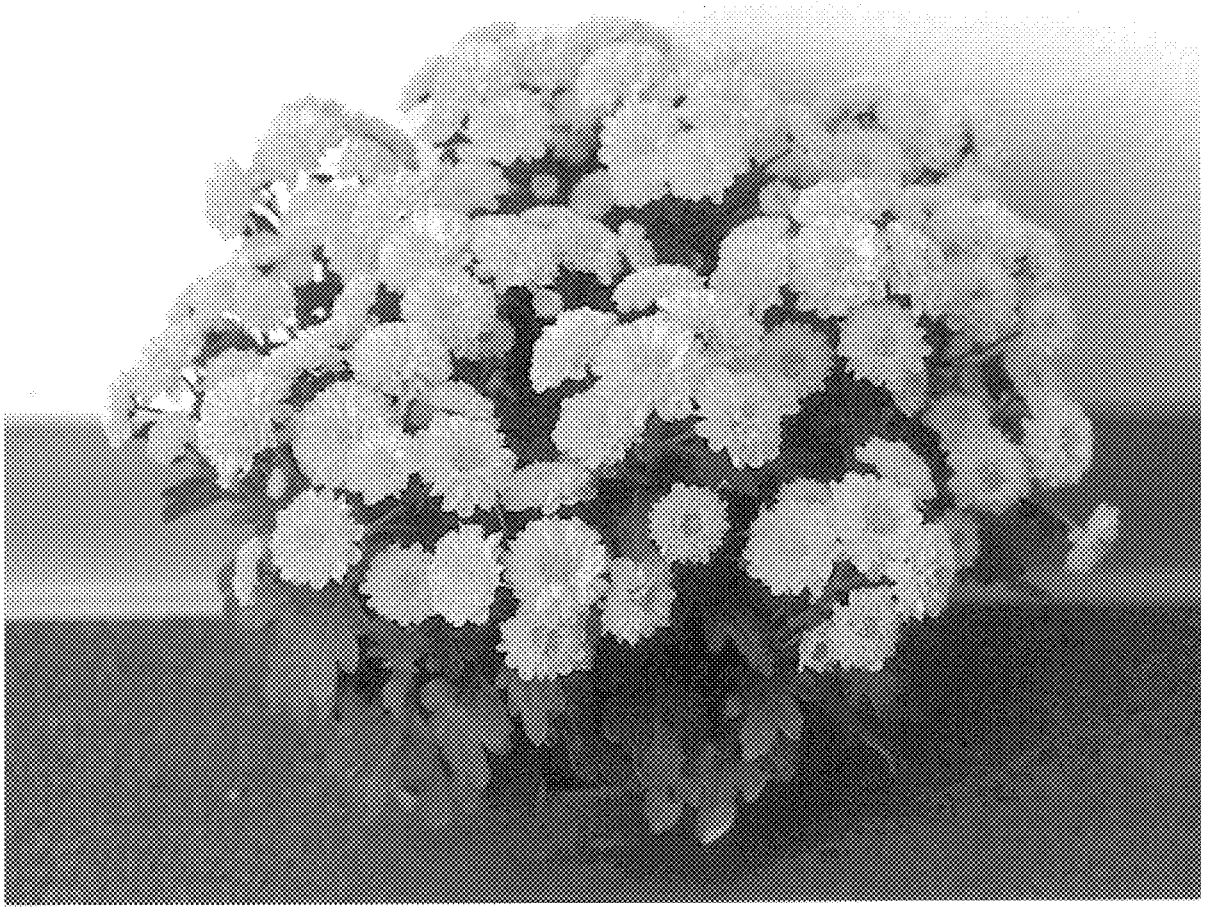

'Gedi One Ost'.

BACKGROUND OF THE INVENTION

The present invention relates to a new and distinct cultivar of Chrysanthemum plant, herein after referred to by the cultivar name 'Gedi One Ost.'

This new cultivar originated from hybridization of a female parent Chrysanthemum cultivar 'Ballino' (U.S. Plant patent application Ser. No. 09/550,159, now abandoned) with a male parent Chrysanthemum cultivar 'Sunny Tripoli' (unpatented in the United States). The new cultivar was discovered by the inventor in October 1996.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'Gedi One Ost' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi One Ost.' These characteristics in combination distinguish 'Gedi One Ost' as a new and distinct Chrysanthemum:

1. Daisy type inflorescence;
2. Consistent flowering response to short days, blooming consistently after 49 days of short day length;
3. Free branching habit;
4. Compact growth habit; and
5. Highly floriferous plants.

Plants of the new cultivar are similar to plants of the parent cultivar, 'Ballino,' in most horticultural characteristics, however plants of the new cultivar differed from plants of the cultivar 'Ballino' in the following characteristics:

1. The new cultivar naturally blooms 1 week later; and
2. The new cultivar has larger diameter blooms.

Plants of the new cultivar are similar to plants of the parent cultivar, 'Sunny Tripoli,' in most horticultural characteristics, however plants of the new cultivar differed from plants of the cultivar 'Sunny Tripoli' in the following characteristics:

1. The new cultivar has more ray florets;
2. The new cultivar has a more round, uniform plant shape; and
3. The new cultivar naturally blooms 1 week later.

The new cultivar can be compared to the Chrysanthemum cultivar 'Yellow Tripoli' (disclosed in U.S. Plant Pat. No. 11,725). However plants of the new Chrysanthemum differed from the plants of the cultivar 'Yellow Tripoli' in the following characteristics:

1. The new cultivar has more ray florets;
2. The new cultivar has a more round plant shape and greater branching;
3. The new cultivar has a shorter internode length; and
4. The new cultivar has more blooms per flowering branch.

BRIEF DESCRIPTION OF THE PHOTOGRAPHS

The photograph shows a plant of 'Gedi One Ost' grown in an 8-inch container. A single cutting was used in the container.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000. The growing conditions range from 60° to 65° F. at night to 70° to 85° during the day. Measurements and numerical values represent averages of typical flowering types.

Botanical classification: *Dendranthema morifolium* cultivar 'Gedi One Ost'.
Commercial classification: Garden-type Chrysanthemum.
Parentage: Hybridization of female parent Chrysanthemum cultivar 'Ballino' (U.S. Plant patent application Ser. No. 09/550,159, now abandoned) with male parent Chrysanthemum cultivar 'Sunny Tripoli' (unpatented in the United States).

PROPAGATION

Time to rooting: 7 to 14 days at approximately 21° C.
Root description: Fine, fibrous.

PLANT

Growth habit: Mounding herbaceous perennial.
Height: Approximately 24.5 cm.
Growth rate: Moderate.
Plant spread: Approximately 27 cm.
Branching characteristics: Free Branching.
Length of lateral branches: Approximately 21 cm.
Number of leaves per lateral branch: Approximately 19.

FOLIAGE

Leaf:
*Arrangement.*—Alternate, single.
*Average length.*—Approximately 4.9 cm.
*Average Width.*—Approximately 3.0 cm.
*Shape of blade.*—Ovate.
*Apex.*—Acuminate.
*Base.*—Attenuate.
*Attachment.*—Stalked.
*Margin.*—Pinnately lobed and toothed.
*Texture of top surface.*—Lightly pubescent.
*Texture of bottom surface.*—Lightly pubescent.
*Color.*—young foliage upper side: Near 147A young foliage under side: Near 147A mature foliage upper side: Near 147A mature foliage under side: Near 147A venation upper side: Near 148B venation under side: Near 147B.
Petiole:
*Average length.*—Approximately 1.3 cm.

BLOOM

Inflorescence:
*Flowering habit.*—Induced by darkness period greater than 13.5 hours, approximately 49 days of appropriate day length required to induce and develop blooms.
*Inflorescence form.*—Daisy.
*Natural flowering season.*—Approximately the last 2 weeks in September.
*Number of inflorescences per stem.*—Approximately 15–30.
*Inflorescence diameter.*—Approximately 3.5 cm.
*Inflorescence depth.*—Approximately 0.8 cm.
*Disc diameter.*—Approximately 1 cm.
*Inflorescence longevity on plant.*—Approximately 26–29 days.
*Persistence.*—Persistent.
Ray florets:
*Appearance.*—Matte.
*Texture.*—Smooth.
*Average number per flower.*—Approximately 90 to 100.
*Shape.*—Cylindric.
*Margin.*—Entire.
*Apex.*—Obtuse.
*Length.*—Approximately 1 cm.
*Width.*—Approximately 0.6 cm.
*Color.*—upper surface at first opening: Near 14A upper surface at maturity: Near 9A upper surface at fading: Near 9B under surface at first opening: Near 14A under surface at maturity: Near 9A. under surface at fading: Near 9B.
Disc florets:
*Appearance.*—Shiny.
*Texture.*—Smooth.
*Average number per flower.*—Approximately 80 to 90.
*Shape.*—Cylindric.
*Apex.*—Obtuse.
*Average length.*—Approximately 0.5 cm.
*Average width.*—Approximately 0.1 cm.
*Color at first opening.*—Near 16A.
*Color at maturity.*—Near 17C.
*Color at fading.*—Near 22A.
Peduncle:
*Length.*—at terminal end (shortest): Approximately 2.5 cm at lateral end (longest): Approximately 4.8 cm.
*Strength.*—Moderate.
*Color.*—Near 147B.
*Habit.*—Erect.
*Surface texture.*—Lightly pubescent.
Inflorescence bud:
*Length.*—Approximately 0.6 cm.
*Diameter.*—Approximately 0.7 cm.
*Form.*—Globular.
*Color.*—Near 5A.
Phyllaries:
*Appearance.*—Matte.
*Texture.*—Lightly pubescent.
*Number.*—Approximately 30 to 40.
*Diameter.*—0.2 cm.
*Length.*—0.4 cm.
*Shape.*—Ovate.
*Margin.*—Entire.
*Apex.*—Acute.
*Color.*—upper side: Near 137B under side: Near 137B.

REPRODUCTIVE ORGANS

Ray florets:
*Pistillate.*—Number of pistils per flower: 1 Stigma shape: 2 branched Stigma color: Near 21A Stigma length: Approximately 0.1 cm.
Disc florets:
*Number of pistils per flower.*—1.
*Stigma shape.*—Cylindric.
*Number of stamens per flower.*—Approximately 5.
*Anther shape.*—Tubular.
*Anther color.*—Near 21A.
*Pollen color.*—Near 21A.
Seed production: Commercially, this plant is not used or observed in a stage wherein seeds would be produced. Therefore, seed production has not been observed to date.

What is claimed is:

1. A new and distinct variety of Chrysanthemum plant named 'Gedi One Ost' as herein illustrated and described.

* * * * *